(12) United States Patent
Watson et al.

(10) Patent No.: US 11,446,089 B1
(45) Date of Patent: Sep. 20, 2022

(54) DEVICE AND METHOD FOR DILATION OF A TUBULAR ANATOMICAL STRUCTURE

(71) Applicant: ENDO UV TECH, Fort Lauderdale, FL (US)

(72) Inventors: Brant D. Watson, Miami, FL (US); Henry W Van Vurst, IV, Fort Lauderdale, FL (US)

(73) Assignee: Photothrombotics, Inc., Fort Lauderdale, FL (US)

( * ) Notice: Subject to any disclaimer, the term of this patent is extended or adjusted under 35 U.S.C. 154(b) by 0 days.

(21) Appl. No.: 17/508,833

(22) Filed: Oct. 22, 2021

(51) Int. Cl.
*A61B 18/24* (2006.01)
*A61M 25/10* (2013.01)
(Continued)

(52) U.S. Cl.
CPC .............. *A61B 18/245* (2013.01); *A61F 2/95* (2013.01); *A61M 25/104* (2013.01);
(Continued)

(58) Field of Classification Search
CPC ....... A61B 18/24; A61B 18/245; A61B 18/22; A61B 2018/2205; A61B 2018/2222; A61B 2018/2244; A61B 2018/2255; A61B 2018/2261; A61B 18/263; A61B 2018/00345; A61B 2018/00351; A61B 2018/00398; A61B 2018/00404; A61B 2018/0041; A61B 2018/00415; A61B 2018/0022; A61B 17/22; A61B 2017/22001; A61B 17/22002; A61B 17/22012; A61B 17/22032; A61B 17/22034; A61B 17/22035; A61B 17/22051; A61B 17/22068;
(Continued)

(56) References Cited

U.S. PATENT DOCUMENTS 4,878,725 A * 11/1989 Hessel ................. G02B 6/4296
606/7
5,151,096 A * 9/1992 Khoury ................ A61N 5/0601
606/7
(Continued)

OTHER PUBLICATIONS

Hasegawa S, Ito H, Toyoda H, Hayasaki Y: Diffraction-limited ring beam generated by radial grating. OSA Continuum 283, vol. 1, No. 2 | Oct. 15, 2018.
(Continued)

*Primary Examiner* — Ahmed M Farah
(74) *Attorney, Agent, or Firm* — Ted Whitlock; Santucci Priore, PL

(57) ABSTRACT

Described is a method and device for dilating a tubular anatomical structure. The device and method can be useful for extracting a blood clot in an artery of a mammal by concentrically irradiating an inner wall of the occluded artery using an ultraviolet (UV) laser beam delivered by an optical fiber having an external or inverted conical tip. Dilation results from photophysical production and release of nitric oxide from the cells lining the arterial wall when UV laser light is projected as a ring beam onto the inner arterial wall. This "minimal contact persistent dilation system" prepares the artery for safer mechanical extraction by thrombectomy, owing to decrease in friction and dissolution of chemical bonding.

25 Claims, 6 Drawing Sheets

(51) Int. Cl.
*A61F 2/95* (2013.01)
*A61B 18/22* (2006.01)
*A61B 17/22* (2006.01)
*A61B 18/00* (2006.01)

(52) U.S. Cl.
CPC .............. *A61B 2017/22068* (2013.01); *A61B 2017/22079* (2013.01); *A61B 2018/0041* (2013.01); *A61B 2018/2261* (2013.01); *A61F 2002/9528* (2013.01); *A61M 2205/053* (2013.01)

(58) Field of Classification Search
CPC ........ A61B 17/22069; A61B 17/22079; A61B 2018/263; A61B 2018/00416; A61B 2018/00422; A61B 2017/22002; A61B 2017/22034; A61B 2017/22035; A61B 2017/22051; A61B 2017/22068; A61B 2017/22069; A61B 2017/22079; A61F 2/95; A61F 2002/9505; A61F 2002/9511
USPC ............ 606/3, 7, 13–15, 17; 607/88, 89, 94; 128/898
See application file for complete search history.

(56) References Cited

U.S. PATENT DOCUMENTS

| | | | | |
|---|---|---|---|---|
| 5,242,438 A | * | 9/1993 | Saadatmanesh | A61B 18/24 606/7 |
| 5,303,324 A | * | 4/1994 | Lundahl | A61N 5/0601 606/7 |
| 5,470,330 A | * | 11/1995 | Goldenberg | G02B 23/26 606/7 |
| 6,539,944 B1 | * | 4/2003 | Watson | A61B 18/20 606/7 |
| 9,149,333 B2 | * | 10/2015 | Harschack | A61B 18/24 |
| 2011/0282330 A1 | | 11/2011 | Harschack et al. | |
| 2014/0074144 A1 | * | 3/2014 | Shrivastava | A61B 17/221 606/200 |
| 2018/0116717 A1 | * | 5/2018 | Taff | A61B 18/1492 |

OTHER PUBLICATIONS

Mnitentag H, Gersten A, Walfisch S: Diamond shaped optical fiber delivery system. Laser Therapy 20.1: 29-34, 2011.

Watson BD, Sadasivan C, Hurst RW: Endovascular Ultraviolet Laser-Facilitated Reversal of Vasospasm Induced by Subarachnoid Hemorrhage in Canines. Acta Neurochir Suppl. 2020;127:127-138. doi: 10.1007/978-3-030-04615-6_19. PubMed PMID: 31407073.

Watson BD, Prado R, Veloso A, Brunschwig JP, Dietrich WD: Cerebral blood flow restoration and reperfusion injury following ultraviolet laser-facilitated middle cerebral artery recanalization in rat thrombotic stroke. Stroke 33: 428-434, 2002.

Watson BD, Dietrich WD, Prado R, Ginsberg MD: Argon laser-induced arterial photothrombosis: characterization and possible application to therapy of arteriovenous malformations. J Neurosurg 66: 748-754, 1987.

Watson B, Sadasivan C, Solomon JA, Hurst RW. Cerebral artery vasospasm in the canine double-hemorrhage model is reversed by endovascular ring beam irradiation with an ultraviolet laser. Abstract 509, Brain 15-0629 (poster), 2015.

Watson BD, Prado R, Morales A, Rose J: Endovascular arterial relaxation facilitated by exposure to coherent ultraviolet (UV) light. Intervent Neuroradiol 11(Suppl 2):185, 2005.

Watson BD, Prado R, Morales A, Rose J: Endovascular carotid artery dilation by ultraviolet laser light transmitted by microcatheterized optical fiber. Abstract Viewer, CD-ROM, Brain 05, abstract 593 (poster), 2005.

\* cited by examiner

Conical-tip optical fiber (d = 100 um)

UV laser ring beam in water

DEVICE AND METHOD FOR DILATION OF A TUBULAR ANATOMICAL STRUCTURE

BACKGROUND OF THE INVENTION

The invention concerns dilation of a tubular anatomical structure, such as a tube or tubule, artery, bronchiole, ureter, vas, or the like, using ultraviolet (UV) laser light to photophysically stimulate release of nitric oxide from smooth muscle cells lining the tubular anatomical structure, resulting in relaxation (radial expansion) of the structure. More particularly, the invention relates to an optical fiber having a conical tip for directing an annular beam of UV light to the inner surface of a tubular anatomical structure.

Four types of approach are currently used for the treatment of occlusive disorders. These include:

(1) use of high-intensity pulsed lasers to disrupt a thrombus or embolus by either ablation or photoacoustic shock (direct ultrasound is also used);

(2) catheterization, angioplasty, and stent emplacement to physically enlarge a vascular lumen constricted by atheroma;

(3) administration of thrombolytic or dethrombosing agents to chemically dissociate a thrombus, often followed by administration of platelet inhibitors (also known as antiplatelet agents) to prevent rethrombosis; and (4) thrombectomy, in which an occlusive thrombus is removed by mechanical extraction, thus restoring blood flow.

Each of these currently available methods is associated with potential harmful effects to the vessel wall. For example, endothelial injury is presently unavoidable during thrombectomy, and provides poor efficacy or dubious quality of recovery in some circumstances.

Two methods are now regarded as sufficiently useful to remove vascular obstructions in a dedicated clinical setting:

(1) aspiration, in which negative pressure is applied proximal to the clot, and (2) extraction by stent retriever (stentriever), in which a mesh network of expanded wires is deployed distal to the clot resulting in direct integration of the clot into the mesh when the retriever is withdrawn, thus removing the clot.

Either of the aspiration or stentriever methods can damage arterial endothelium and arterial wall layers in different but characteristic ways, which portend future negative consequences for arterial structure and function. To this point, the main focus has been on quick removal of a clot by these mechanical means, with much less regard for local or peripheral damage, especially to the ordinarily antithrombotic endothelium. All refinements to these methods have been limited strictly to mechanical improvements in aspiration suction efficiency, or integrability of a stentriever with a clot, in an effort to remove the entire clot with one application (pass) of the device. Despite the apparent recent success of thrombectomy in removal of arterial occlusions, these current procedures are not perfected. Arterial endothelium can be damaged by mechanical friction during clot extraction. Rupture of the vessel is a known risk of any one of the currently used interventional procedures, such as an aspiration catheter or stentriever, and arterial wall perforation can occur during catheter insertion, especially when accessing entrance to branch arteries. Furthermore, patient recovery following thrombectomy is rather poor, especially behaviorally. About 60% of patients exhibit signs of residual damage, but this has become an area of concern only recently because the principal focus of practitioners has been on the technicalities of clot extraction. In this context, recovery is compromised if extraction is inefficient (requiring up to five passes, thus much more mechanical interaction with the vessel wall).

Methods have been proposed to address the damage and risk problems resulting from previously known procedures. For example, U.S. Pat. No. 6,539,944 described the use of ultraviolet (UV) laser light, with or without additional pharmaceutical agents, to dissolve an occlusive thrombus in an artery. In other words, the UV laser light, itself, was used to facilitate dissolution of the thrombus, by means of its photophysical production of the thrombin inhibitor, nitric oxide (NO.), a free radical which destabilizes adjacent platelet aggregates when secreted from irradiated smooth muscle cells in the arterial wall. This patent is incorporated herein by reference, in its entirety.

What is needed in the art is a device and method for dilating a tubular anatomical structure containing smooth muscle cells during treatment of a patient while mitigating and minimizing the damage to the anatomical structure and lowering the risk of consequent harm to the patient when undergoing a medical procedure. This can be done with a dilation system in accordance with the subject invention. Preferably, the system of the invention can minimize the contact between the mechanical device of the system and the anatomical structure being dilated, thereby providing a minimal-contact dilation system. For example, thrombectomy using an aspiration catheter, stentriever, or other mechanical thrombus extractor can be effected more easily with less endothelial damage when prepared by a such a system, in which UV laser light and not mechanical pressure directly induces dilation of the occluded artery. Preparing an artery in this manner for a subsequently deployed thrombectomy device facilitates a reduction in friction and chemical bonding, and thus less mechanical damage to the arterial wall before, during and after clot withdrawal.

BRIEF SUMMARY OF THE INVENTION

The subject invention is particularly useful for dilation of an artery using an optical fiber capable of delivering UV light in the form of an annular laser beam to the arterial wall, to reverse vasospasm consonant with hemorrhagic stroke, or facilitate removal of a blood clot (thrombus) from vasculature. A method of dilating a tubular anatomical structure using a conically tipped optical fiber to produce the annular shape and deliver the laser beam to the inner wall of a tubular anatomical structure is also part of this invention.

The device and method can be particularly applicable in thrombectomy procedures performed on a partially or fully occluded artery, in treating stroke, myocardial infarction, and other vascular occlusive disorders, particularly thrombi formed within the vasculature of the brain. It may also be applicable to dissolving distal microvascular thrombi known to occur in hemorrhagic stroke as a manifestation of "early brain injury."

The subject invention therefore includes a fused silica optical fiber for carrying UV laser light, wherein the optical fiber has a distal end, wherein the distal end is configured as an inverted cone (i.e., a negative conical lens) or an everted cone, both capable of emitting the UV laser light as a conical beam. The emitted conical beam of UV laser light impinges on an inner wall of a tubular anatomical structure in a ring-shaped or annular configuration.

The conical distal end of the optical fiber can be provided as a tip which is separate from, i.e., is not part of, the optical fiber, per se, but is optically coupled, and preferably physically coupled, to and contiguous with the distal end of the optical fiber such that the tip is in optical communication with the optical fiber. Preferably, the tip is configured having a distal end formed as an everted cone capable of emitting the UV laser light as a conical beam.

Preferably, the optical fiber of the invention, or the tip coupled thereto, can comprise diamond at its distal end to optimize the emission of the conical beam, e.g., the size, shape, emission angle, or intensity of the beam can be modified and even improved by use of diamond as the material for the tip, or a diamond-like material, such as zirconium oxide. Alternatively, the tip can be comprised of an ultraviolet-transparent, high index of refraction specialty plastic.

A preferred embodiment of the optical fiber tip of the invention is in the shape of an inverted cone (e.g., a negative axicon) capable of emitting into water an annular beam at an emission angle β up to 56° from a central longitudinal axis of the optical fiber. An everted conical tip can emit light at an angle β up to 71.5°. These angles are necessarily approximations because the natural angular spread of a laser beam may exceed the critical angle for total internal reflection, thus decreasing some portion of the beam power The larger the angle allowed by Snell's Law, the thinner the projection of the ring beam on the irradiated surface, with a correspondent increase in laser intensity. Preferably, the inverted conical tip is capable of emitting into water an annular beam at an emission angle β of 20° to 56° from a central longitudinal axis of the optical fiber; with the external cone the limit of the emission angle range is 71.5°. With this angle of emission, the optical fiber or tip of the invention is capable of emitting an annular beam onto an inner wall of a tubular anatomical structure.

The invention further concerns a dilation system comprising a thrombectomy catheter modified as a system which employs an optical fiber for carrying UV laser light, the optical fiber having a distal end or comprising a tip at its distal end, wherein the optical fiber or tip is configured in a conical shape for emitting the UV laser light as a conical beam. The dilation system comprising an optical fiber of the invention can have a distal end or tip of the optical fiber configured as an inverted (protruding inwardly) cone or an external projecting cone. The dilation system comprising an optical fiber of the invention can be employed using an aspiration thrombectomy catheter or a stentriever. Preferably, the dilation system of the invention minimizes physical contact with the dilated anatomical structure but still allows impingement of UV laser light onto the structure. Because the impingement and resulting dilation can be persistent, a preferred embodiment of the invention is referred to as a "minimal contact persistent dilation system." The preferred embodiments of the system therefore comprise a "minimal contact persistent dilation system."

In use, the dilation system of the invention can be employed in a method for dilating a tubular anatomical structure in a body of a patient. A method according to the subject invention comprises the steps of:
  providing a catheter housing a UV-transparent balloon expanded with a UV-transparent gadolinium-based contrast agent in which an optical fiber for carrying UV laser light is inserted, wherein the optical fiber has a distal end or tip having a conical configuration; and
  emitting UV laser light energy through the balloon (which is expanded by the gadolinium contrast agent to be contiguous with the inner wall of the tubular anatomical structure) as an annular beam onto smooth muscle cells in the inner wall of the tubular anatomical structure. This will stimulate photophysical production and release of nitric oxide (NO.) from stores of nitrites ($NO_2^-$) in arterial smooth muscle cells, whereby the nitric oxide causes relaxation of the smooth muscle cells and dilation of the tubular anatomical structure.

The method can be adapted or applied in an endovascular thrombectomy procedure further comprising the steps of:
  positioning the UV-fiberoptic dilation system within about 1-10 vessel diameters of a clot within an artery containing a clot;
  expanding the UV-transparent balloon catheter with UV-transparent gadolinium contrast fluid up to the inner wall of the artery enough to stop blood flow but not to dilate the artery by mechanical pressure,
  emitting a burst of UV light energy as a laser beam through the gadolinium-expanded balloon wall and onto smooth muscle cells in the wall of an artery to stimulate the production of NO. from stores of nitrites ($NO_2^-$) in smooth muscle cells, whereby active dilation of the artery is stimulated and can be observed; and
  removing the clot.

A UV-transparent balloon catheter is first deployed into the tubular structure to center the conical tip of the inserted optical fiber, so as to ensure uniform irradiation intensity around the circumference of the structure. The balloon can be expanded up to the inner diameter of the tubular structure with a UV-transparent gadolinium contrast agent to ensure visibility on x-ray examination. UV irradiation is then conducted through the balloon fluid and into the wall.

The method of the invention is preferably carried out by directing the UV light onto the vessel wall within about 1 and about 4 vessel diameters removed from the clot. The method can be carried out using continuous UV light emission, or the UV light emission Q-switched (pulsed) acousto-optically at high frequency (5-25 kHz) with pulse widths greater than 50 nanoseconds, or as a quasi-continuous beam with picosecond pulse widths, e.g., pulsed at 100 MHz with a pulse width of >10 psec, or as a square wave for at least 2 up to 10 seconds. In a preferred embodiment, the UV light is emitted at a wavelength of about 180-400 nm, more preferably at a wavelength of about 300-400 nm. One preferred embodiment emits the UV light using a frequency-tripled Nd:YAG laser which emits light at 355 nm. A preferred incident intensity of the UV light is between about 3 and about 20 watts per square centimeter.

In accordance with the methods described herein, it would be understood that the thrombectomy catheter used in the thrombectomy procedure can be an aspiration catheter or a catheter through which a stentriever is inserted.

It is an object of the invention to provide a less invasive or damaging method for extracting a thrombus from an artery of a mammal by non-mechanically opening a larger diameter path for the invasive interventional device, as well as for the withdrawn thrombus to exit through. This and other objects of the invention are provided by one or more of the embodiments described herein.

An object of the invention is to optimize arterial integrity during and after thrombectomy by reducing frictional or chemical binding resistance to mechanical extraction of the occlusive clot. A device and method of the subject invention comprises providing suitably intense UV laser irradiation of the arterial inner wall proximal to a clot when employing an aspiration catheter, or distal to a clot when employing a stentriever, when performing a thrombus extraction technique. UV laser irradiation by a ring-shaped beam whose axis is collinear with the artery induces evident dilation of the arterial wall within seconds, wherein the dilation effect will propagate proximally and distally to weaken frictional and/or chemical binding of the clot to the wall.

Another object of the subject invention is to provide an aspiration catheter or stentriever further comprising an optical fiber capable of carrying UV light to the distal end or tip of the catheter, wherein UV light can be emitted for a brief period of time, e.g., 2-10 seconds during saline flush or expansion of a balloon catheter to clear blood from the vascular wall (but not to mechanically dilate the artery), and thus directed to the smooth muscle cells comprising the wall of the vessel. One particular embodiment introduces the laser beam through an endovascularly deployed optical fiber comprising a protruding (external) conical tip which by one reflection and one refraction can serve, in effect, as a diverging lens for the beam. This design will produce a circumferential irradiation pattern as an expanding conical ring, producing an annular beam of laser light on the wall of the tubular anatomical structure onto which the beam is directed. The protruding conical output tip is preferably made using a UV-transparent material with a higher index of refraction, n, than fused silica, such as diamond, zirconium oxide, or a custom plastic with n>2, which can be optically coupled to the silica. As the exit angle $\beta$ is increased, the beam intensity and efficiency of arterial dilation are also increased concomitant with a decrease in length of beam projected along the arterial wall, because the ring-shaped area irradiated is also decreased. Any projection length along the arterial wall will elicit dilation if the intensity criterion is met, but a larger beam exit angle facilitates more intensity and thus more efficient use of the beam.

The UV ring beam intensity around the arterial circumference is intended to be constant, to ensure reproducibility of the procedure. This is facilitated by centering the optical fiber with a UV-transparent balloon catheter. If the structure is an artery, the expanded balloon seals off blood flow but does not itself expand the artery. The arterial wall is then irradiated through the balloon wall, in minimal contact with the artery.

These same considerations apply to the inverted conical tip as well, but in diamond the maximum emission angle (e.g., ca. 56°) will be less than that from the external tip (e.g., 71.5°). The intent is to provide two different ways to produce beams in the shape of an expanding ring, the relative benefits of which have been described above and can be assessed for clinical application.

DETAILED DESCRIPTION OF THE INVENTION

The subject invention relates to a device and method for dilation of a tubular anatomical structure, such as an artery, wherein the dilation is induced by directing a suitably intense ultraviolet (UV) laser beam onto the wall of the tubular anatomical structure which does not functionally damage the cells of that structure. The device, system or method of the invention can be useful in anatomical structures, such as an anatomical canal, tube or tubule, blood vessel, such as artery, bronchiole, ureter, vas, or the like.

A preferred embodiment employs a fused silica optical fiber comprising an inverted conical tip. The tip preferably comprises a UV-transparent material with a high index of refraction in optical contact with the fused silica optical fiber. A UV-transparent and very hard material with high refractive index, such as diamond (index of refraction at 355 nm of 2.48) or zirconium oxide (index of refraction at 355 nm of 2.3), or custom-designed high index (n>2) plastic, is preferred for the tip. Such a tip can provide the capability to produce exit angles (half-conical angles) of the UV ring beam of up to 56° (using an inverted conical tip) or 71.5° (using an everted conical tip), both made of diamond.

One preferred embodiment of the subject invention concerns an optical fiber, preferably with a core 10 to 100 um, more preferably 50-100 um, in diameter for transporting UV laser light to a distal end or tip of the optical fiber and emitting a conical beam of UV laser light which impinges onto an inner wall of a tubular anatomical structure in the form of an expanding annular ring or ring-shaped beam.

Figure 1A:
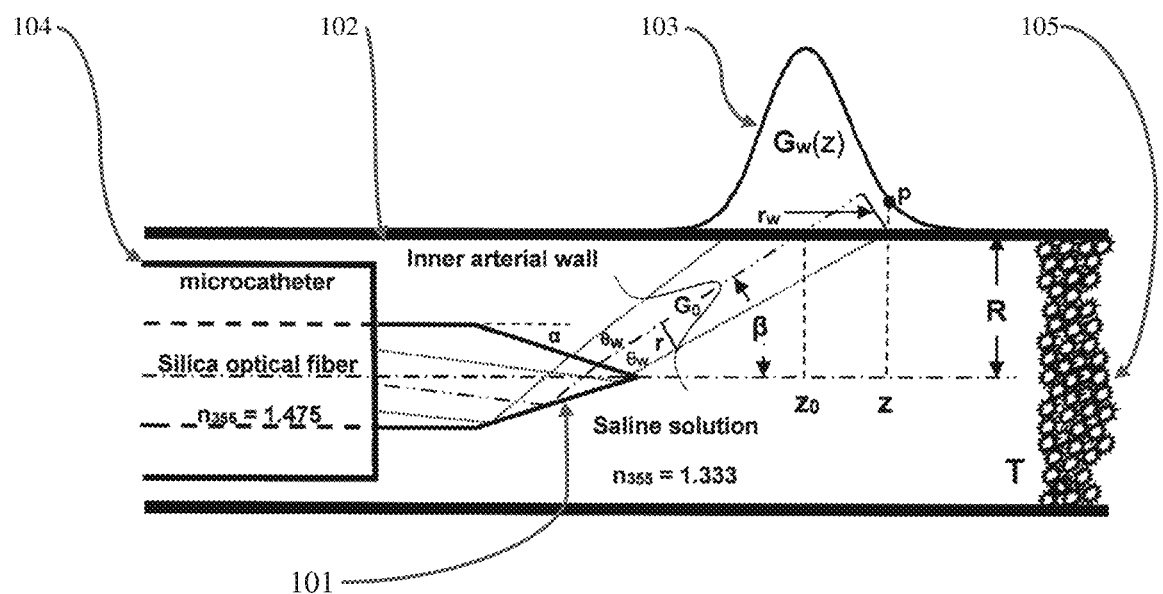
FIG. 1A shows the upper half of a z-plane cross section of a laser ring beam with a gaussian intensity distribution $G_0$ (produced by an optical fiber with an external conical tip, with cone half angle $\alpha$) as it impinges onto the inner wall of an artery of radius R to produce the expanded gaussian beam profile G. Note the beam has a polar angle spread of $2\theta_w$. The ring beam is cylindrically symmetric about the optic axis, with its central maximum emitted at the angle $\beta$. The intensity profile of $G_0$ is drawn to 1/9 scale. The intensity of $G_w$ at point "p" is a function of $r_w = (z-z_o)\sin\beta$, as well as of $(z^2+R^2)^{1/2}$.

To achieve this ring-shaped beam formation, the distal end of a fused silica optical fiber can be formed in a conical shape, e.g., an external conical shape (projecting outwardly), or can be an inverted conical shape (projecting inwardly.) As illustrated in FIG. 1A using a silica optical fiber having an external conical tip 101 positioned within a microcatheter 104, the upper half of a z-plane cross section of a laser ring beam is shown with a gaussian intensity distribution, $G_0$, produced by an optical fiber with an external conical tip with cone half angle $\alpha$. The distribution $G_0$ impinges onto the inner wall 102 of an artery having a radius R to produce the expanded gaussian beam profile $G_w$ 103. Note the beam has a polar angle spread of $2\theta_w$. The ring beam is cylindrically symmetric about the optic axis, with its central maximum emitted at the angle $\beta$. The intensity of $G_w$ at point "P" is a function of $r_w = (z-z_o) \sin \beta$, as well as of $(z^2+R^2)^{1/2}$. As illustrated, the optical fiber 101 is positioned proximal to a thrombus 105(T) for use.

Figure 1B:
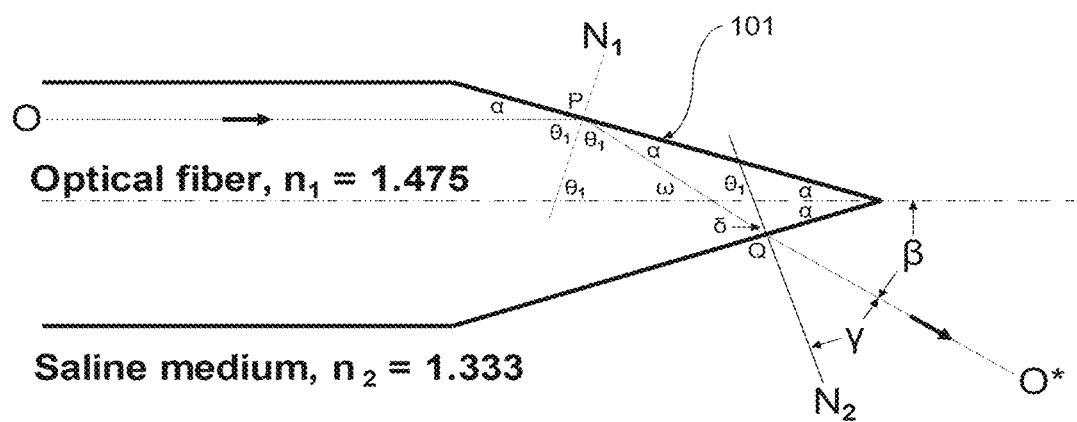
FIG. 1B shows laser axial ray tracing in a protruding (external, or everted) conical-tip optical fiber. The dotted line (OO*) traces the path of an idealized ray of laser light in a silica optical fiber with a conical tip (total apex angle=$2\alpha$) at the output end. The beam obeys total internal reflection at point P, as long as the angle of incidence $\theta_1$ is greater than the critical angle $\theta_{crit}$ (64.653°) at the silica/water interface (and thus by inspection $\alpha<90°-\theta_{crit}$), and then emerges from point Q into a water-based medium, $\theta_{crit}=64.653°$. The locus of points defined by O* when rotated about the optic axis yields a beam in the shape of a ring. $N_1$ and $N_2$ are normal lines to the top and bottom surfaces of the cone. From the diagram, $\alpha+\theta_1=90°$ and $\omega=180°-2\theta_1$ by inspection, thus $\delta=3\theta_1-180°=90°-3\alpha$. The ring beam locus is a conical surface defined by angle $\beta(\alpha)=\theta_1-\alpha-\gamma(\alpha)$, also by inspection. $\gamma(\alpha)$ is expressed as $\sin^{-1}\{(n_1/n_2)\cos 3\alpha\}$. From Snell's Law, $\beta(\alpha)$ can now be determined as a function of the half-angle $\alpha$ of the fiber conical tip.

FIG. 1B is a detailed view of a fused silica optical fiber having an external conical tip 101 shown in FIG. 1A, illustrating a laser axial ray tracing in a protruding (external) conical-tip optical fiber. The dotted line (OO*) traces the path of an idealized ray of laser light in a silica optical fiber with a conical tip (total apex angle=$2\alpha$) at the output end. The beam obeys total internal reflection at point P, as long as the angle of incidence $\theta_1$ is greater than the critical angle $\theta_{crit}$ (64.653° at the silica/water interface (and thus by inspection $\alpha < 90° - \theta_{crit}$), and then emerges from point Q into a water-based medium, $\theta_{crit}$=64.653°. The locus of points defined by O* when rotated about the optic axis yields a beam in the shape of a ring. $N_1$ and $N_2$ are normal lines to the top and bottom surfaces of the cone. From the diagram, $\alpha + \theta_1 = 90°$ and $\omega = 180° - 2\theta_1$ by inspection, thus $\delta = 3\theta_1 - 180° = 90° - 3\alpha$. The ring beam locus is a conical surface defined by angle $\beta(\alpha) = \theta_1 - \alpha - \gamma(\alpha)$, also by inspection. $\gamma(\alpha)$ is expressed as $\sin^{-1}\{(n_1/n_2) \cos 3\alpha\}$. From Snell's Law, $\beta(\alpha)$ can now be determined as a function of the half-angle $\alpha$ of the fiber conical tip.

Figure 2A:
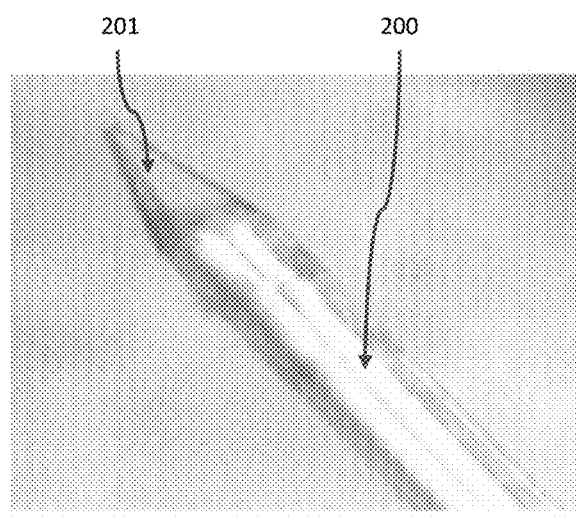
FIG. 2A illustrates an external conical tip machined on a 36° full apex conical angle ($2\alpha$) fused silica fiber according to an embodiment of the invention.

FIG. 2A is a photograph of an optical fiber 200 in accordance with the subject invention, illustrating an external conical tip 201 on a 36° full apex conical angle (2$\alpha$) fused silica fiber according to an embodiment of the invention.

Figure 2B:
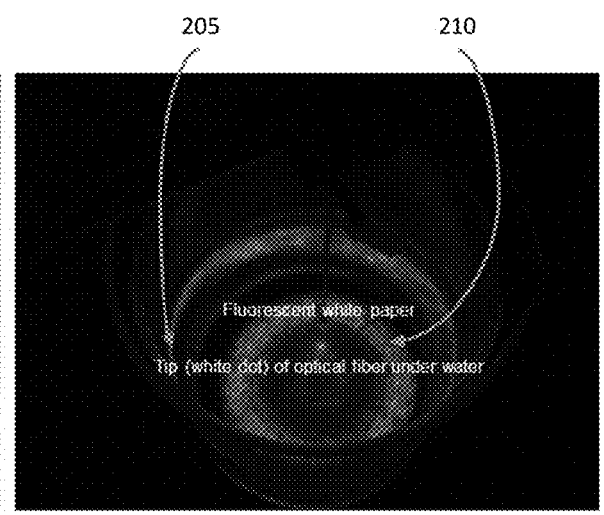
FIG. 2B illustrates a UV laser ring beam generated in water by the external conical tip shown in FIG. 2A. Table 1 shows values of $\alpha$, $\beta(\alpha)$ and the reflection and refraction angles for a pure silica optical fiber, and Table 2 shows $\beta(\alpha)$ when the tip is optically coupled diamond. The range and values (up to 71.5°) of $\beta(\alpha)$ are considerably increased for diamond compared to silica itself (up to 48.4°).

FIG. 2B illustrates a UV laser ring beam generated in water within a glass container 205 by the optical fiber having an external conical tip shown in FIG. 2A. The ultraviolet laser beam is transformed into an expanding ring shape 210, as shown in FIG. 2B as a diffuse ring on fluorescent paper; the ring beam can then irradiate the inner circumference of an artery after displacement of blood using a UV-transparent balloon filled with UV-transparent gadolinium-based contrast medium.

Table 1, herein below, provides the range of paths of beams in a fused silica external conical tip in terms of the fiber half conical angle $\alpha$, and the angles associated with one total internal reflection and one refraction, resulting in the beam exiting the tip at angle $\beta(\alpha)$. The ring beam cross section along the arterial wall (angular width $2\theta_w$, cf. FIG. 1A) can vary from gaussian to a super gaussian "top hat" profile, a typical output pattern for a multimode optical fiber, which at maximal expression means essentially constant intensity over the ring width. These intensity patterns are not critical to production of dilation, but they do affect the average and peak powers of the beam and their upper limits.

An external projecting conical tip according to an embodiment of the invention is illustrated in FIGS. 1A, 1B, and 2. A sharp external conical tip (full apex angle <40°, half conical angle <20°; cf. FIGS. 1 and 2A) made of silica may be subject to fracture and/or entanglement by an endovascular obstacle (if any). A maximally blunt external silica tip (full apex angle ca. 50°) is preferable (cf. Table 2.) Fracture can be avoided with a tip made of a very hard material such as diamond, zirconia, or a high refractive index (n>2) plastic, but entanglement may still be possible, depending on the array of complementary devices used. In practice, optical fibers are introduced through catheters, which offer protection.

Figure 3:
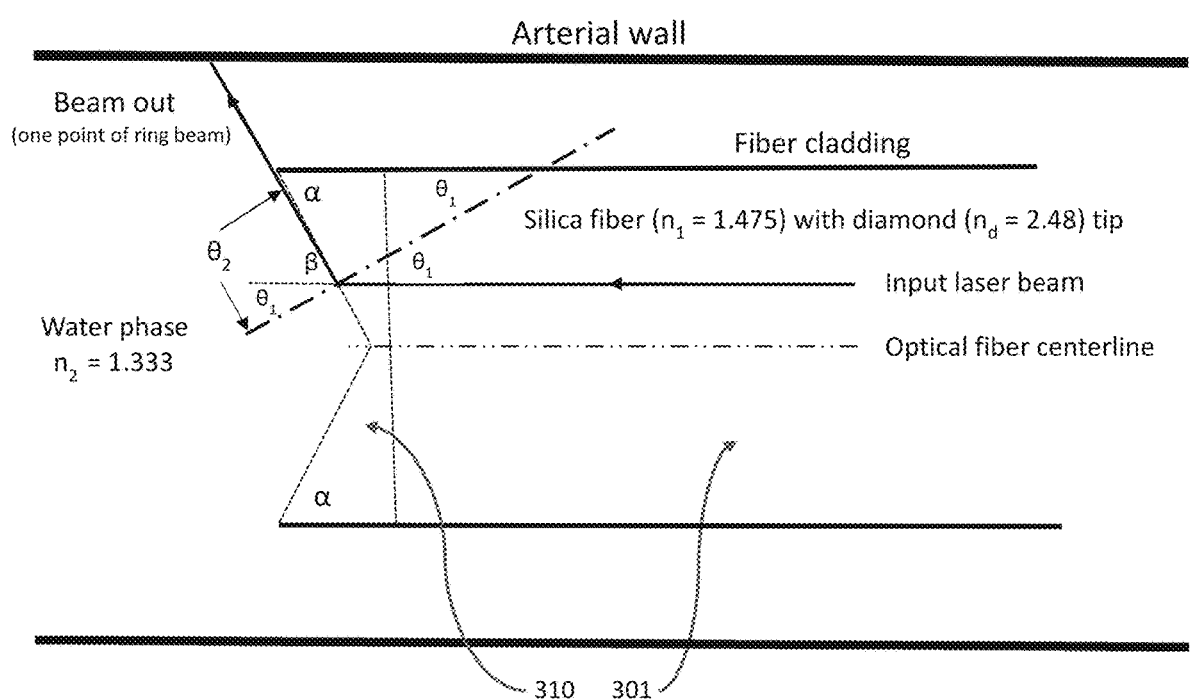
FIG. 3 shows optical properties of an inverted conical tip optical fiber, showing paths of reflected and refracted laser light (entering from right side) in a fused silica fiber with an inverted conical tip or a tip made from diamond, with the beam exiting into water (saline) onto the inner arterial wall. The maximum angle of emission $\beta(\alpha)$ from diamond into water is ca. 56°, which far exceeds that from silica only (25.4°); cf. Table 3.

Alternatively, the conical tip can be inverted (inwardly projected) at the distal end of the optical fiber as shown in FIG. 3. Preferably, the fused silica optical fiber 301 comprises an inverted diamond conical tip 310 because this design can avoid being entrapped by an endovascular obstacle, and is less likely to be damaged during insertion or deployment. Such a tip is capable of emitting an annular (ring-shaped) beam into water at an emission angle of up to 56° using a diamond tip (cf. Table 3.) A fused silica conical tip can produce emission angles of between 20° and 24° (cf. Table 3) relative to the central longitudinal axis of the optical fiber. The beam intensity and the efficiency of the dilation (and associated clot dissolution) process increase with the emission angle, so it is desirable to maximize it within the physical limits permitted by a UV-transparent, high refractive index fiber tip material (fused silica, diamond, zirconia, or custom plastic). The tip can be made from a UV-transparent, high refractive index (n>2) material coupled to a conventional optical fiber, wherein the coupled tip and optical fiber are in optical communication with one another. The coupled conical tip of a silica optical fiber can project outwardly (protrude) from distal end of the optical fiber and emit a ring beam at an angle up to ca. 48° relative to the longitudinal axis of the optical fiber (Table 1). If the tip is composed of diamond (Table 2), a much wider range of emitted angles up to ca. 71.5° can be realized.

An optical fiber comprising a conical tip—projecting outwardly (everted) or inwardly (inverted)—can be employed in a minimal contact persistent dilation system of the invention, for example, as part of a subsequently deployed arterial thrombectomy catheter system. The width of the annular or ring beam emitted by an optical fiber of the invention is dependent on the arterial diameter. This feature can be advantageous because the dilation effect in any tubular anatomical structure, including an artery, is driven by beam intensity and can occur very quickly (<1 second) depending on the nitric oxide (NO.) concentration produced photophysically in the cells lining the tubular anatomical structure, e.g., an arterial wall. Irradiation at a given intensity will induce a corresponding dilation, which can propagate itself proximally and distally from the area contacted by the annular beam via transnitrosation.

In a preferred embodiment, an optical fiber comprising an inverted conical tip or a blunt, everted conical tip can be utilized with a balloon catheter comprising a UV-transparent balloon in combination with an aspiration thrombectomy catheter. Preferably, the guidewire introduced in the segment proximal to an occlusion can be centered with a UV-transparent balloon catheter and expanded with a UV-transparent gadolinium-based contrast agent, whereupon the guidewire is replaced by the optical fiber.

Another preferred embodiment is a dilation system of the invention comprising an inverted conical tip or blunt everted conical tip combined with a balloon catheter and used in sequence with a stentriever. In this embodiment, the guidewire makes the initial penetration, where it must be centered in the expanded balloon catheter and then replaced by the optical fiber in order for the UV ring beam to properly impinge on the inner wall at a uniform circumferential intensity.

Another aspect of the invention concerns a method for performing an endovascular thrombectomy procedure, wherein the method comprises the steps of:
  providing a thrombectomy catheter compatible with a UV-compatible optical fiber;
  expanding the UV-transparent balloon catheter with UV-transparent contrast fluid up to the inner wall of the artery, enough to stop blood flow but not to dilate the artery by mechanical pressure;
  positioning the UV-fiberoptic thrombectomy catheter within one to four vessel diameters of a clot contained within the vessel;
  emitting UV light energy as a ring beam onto smooth muscle cells in the inner wall of an artery to induce formation and release of nitric oxide (NO.) and thereby cause dilation of the artery, regardless of whether the endothelium (the usual source of NO.) is intact, and whether blood is present or not; and
  removing the clot.

The above procedure can be carried out in preparation for use of an aspiration catheter or a stentriever.

Figure 4A:
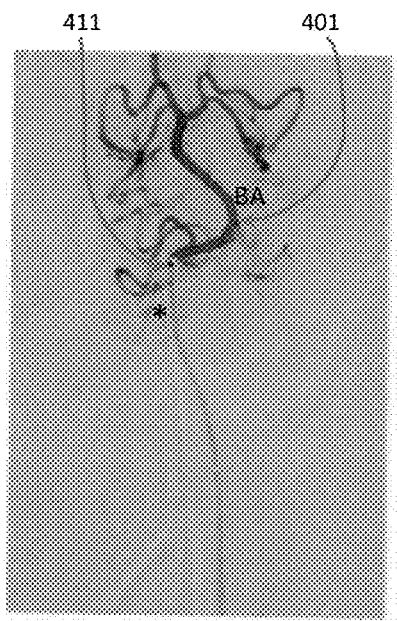
FIGS. 4A, 4B, and 4C show emplacement of optical fiber tips and endovascular UV irradiation in basilar arteries (BAs) of three dogs. Dilation caused by UV irradiation is semi-local; for basilar artery lengths of ~40 mm, the dilation can spread up even to 60 mm from the locus of ring beam irradiation of an adjoining (vertebral spinal) artery.
Figure 4B:
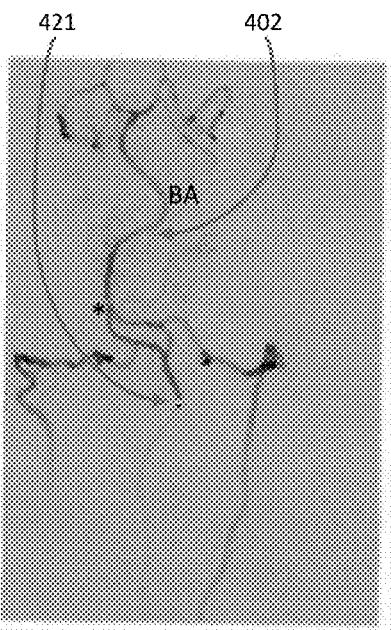
Figure 4C:
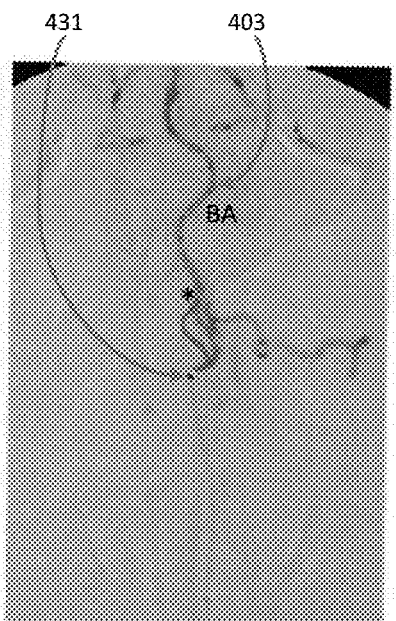

FIGS. 4A, 4B, and 4C show the deployment of our fiber optic device to effect endovascular 355 nm UV laser irradiation in basilar arteries (BAs) 401, 402 and 403 at baseline of three dogs, respectively (BA origin designated by * for each). Dilation caused by subsequent UV irradiation is semi-local; for basilar artery lengths of ~40 mm, the dilation can spread up to 60 mm from the locus of ring beam irradiation of an adjoining (vertebral spinal) artery (FIGS. 4B and 4C). FIGS. 4B and 4C indicate that vertebral spinal artery constriction prevented access of the fiber tip to the mouth of the basilar artery before UV irradiation. Although for dog A the fiber tip 411 could be placed 22% distal to the BA origin, which is optimal, for dogs B and C the fiber tips 421 and 431 could be only placed within 52% and 34% of the respective BA length proximal to its origin (*). For irradiation intensities of 12–20 watts/cm$^2$, average dilation proceeded to 94% of baseline after starting from 78%, and while decreasing linearly over the 40 mm range, dilation was still observed at the BA termini.

Figure 5:
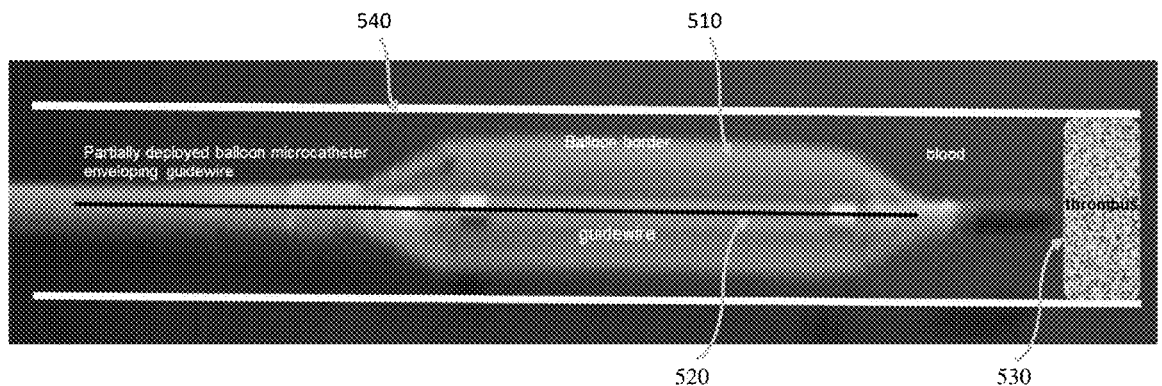
FIG. 5 shows initial deployment of a balloon catheter over guidewire (dark gray) inserted near an arterial occlusion (thrombus) before UV laser-facilitated thrombectomy. The balloon is partially inflated. When the balloon is or nearly inflated, the guidewire will be effectively centered in the artery. At this point, the guidewire can be withdrawn and replaced with a UV emitting optical fiber in order to dilate an impeding tortuosity (if present) to decrease resistance to further insertion of the guidewire, in order to further trace the optimum route through the artery for the UV emitting optical fiber and then the thrombectomy device.

FIG. 5 shows initial deployment of a balloon catheter 510 over guidewire 520 inserted near an arterial occlusion (thrombus) 530 before UV laser-facilitated thrombectomy. The balloon is partially inflated (shown here as not contacting the inner wall of the artery 540.) When the balloon is or nearly inflated, the guidewire will be effectively centered in the artery. At this point, the UV emitting optical fiber can replace the guidewire and dilate an impeding tortuosity (if present) to decrease resistance to the guidewire, and the guidewire can temporarily replace the UV fiber in order to further trace the optimum route through the artery toward the thrombus, before reinsertion of the UV fiber followed by the thrombectomy device.

Figure 6:
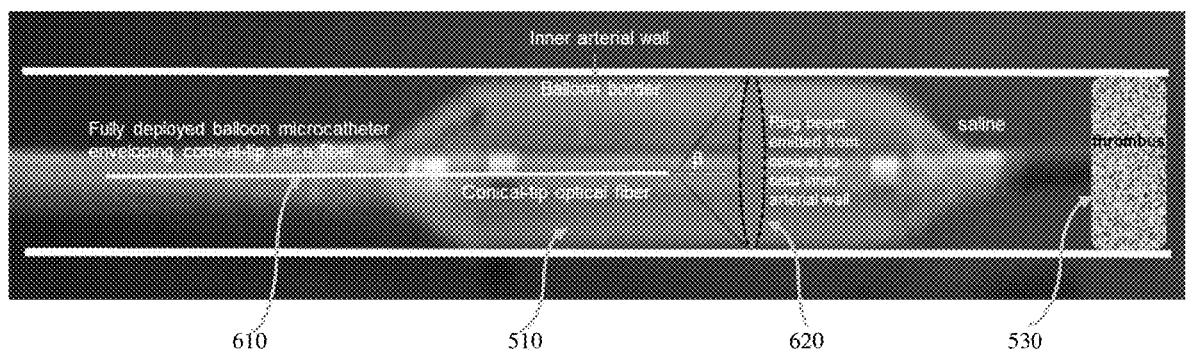
FIG. 6 shows the balloon catheter of FIG. 5 which has been fully inflated over the centered guidewire, and the guidewire withdrawn and replaced by an optical fiber (white line) which will emit UV laser light from a conical tip synthesized to produce a ring beam (elliptical locus of hashmarks) at the angle $\beta$ desired near an occlusion (thrombus). The output end of the fiber may be placed as close to the thrombus as permitted by the balloon, but UV ring beam irradiation will elicit persistent arterial dilation beginning from <4 up to 40 diameters away from the thrombus. At beam intensities from 3-20 watts/cm$^2$, dilation will occur in seconds and will extend into the thrombosed segment. The balloon is then deflated and withdrawn, and the thrombectomy device installed over the optical fiber now used as a guidewire (although practitioners may prefer to replace the optical fiber with a standard guidewire and then withdraw the balloon). In the above configuration, an aspiration catheter would be introduced to withdraw the thrombus, now with less frictional resistance because the occluded arterial segment is dilated. To deploy a stentriever, a guidewire must penetrate the thrombus, likely near the edge, and balloon deployment over it and other steps would occur as described. Here the dilation distal to the thrombus will allow the stentriever to be deployed at a larger diameter, ensuring maximal interception of the thrombus and complete extraction so long as stentriever integrability is preserved.

FIG. 6 shows the balloon catheter 510 of FIG. 5 fully inflated over the guidewire, centering it, and the guidewire has been replaced by an optical fiber 610 which will emit UV laser light from a conical tip capable of producing a ring beam 620 at the angle β desired. The output end of the fiber may be placed as close to the thrombus 530 as permitted by the balloon, but UV ring beam irradiation will elicit persistent dilation beginning from <4 up to 40 diameters away from the thrombus. At beam intensities from 3-20 watts/cm$^2$, dilation will occur in seconds and will extend into the thrombosed segment. The balloon is then deflated and withdrawn, and the thrombectomy device installed over the optical fiber now used as a guidewire (or more likely, the optical fiber is replaced by the initial guidewire according to surgeon preference). In the above configuration, an aspiration catheter would be introduced to withdraw the thrombus, now with less frictional resistance because the occluded arterial segment is dilated. To deploy a stentriever, a guidewire must penetrate the thrombus, likely near the edge, and balloon deployment over it and other steps would occur as described. Here the dilation distal to the thrombus will allow the stentriever to be deployed at a larger diameter, ensuring maximal interception of the thrombus and complete extraction so long as stentriever integrability is preserved.

Figure 7:
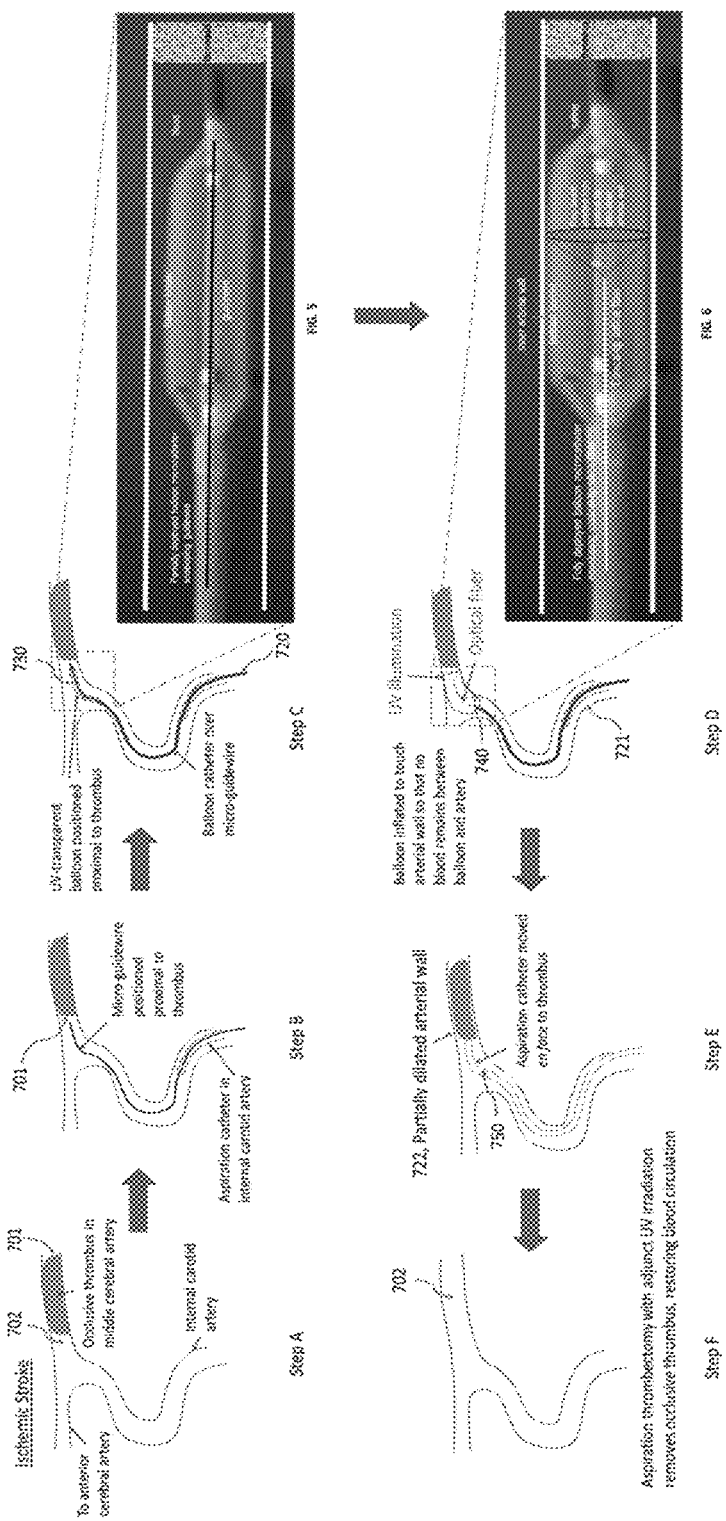
FIG. 7 offers a pictorial summary of the application to thrombectomy of ultraviolet laser-induced dilation in order to minimize wall damage due to mechanical friction.

FIG. 7 offers a pictorial summary of the steps employed the application of the invention to thrombectomy of ultraviolet laser-induced dilation in order to minimize wall damage due to mechanical friction. FIG. 7 illustrates the steps of the method of the invention carried out using a balloon catheter illustrated in FIGS. 5 and 6. In step A of FIG. 7, the thrombus 701 is shown to be in a middle cerebral artery 702, prior to deployment, of a thrombectomy catheter of the invention. A micro-guidewire 720 typically employed in a balloon catheter, is fed through the internal carotid artery 721 and positioned proximal to the thrombus 701 (step B). In step C, the UV-transparent balloon 730 is then fed over the micro-guidewire 720, as in normal use of the device, and also positioned proximal to the thrombus 701. Step D illustrates that the balloon catheter is then inflated 740 to contact the inner wall of the vessel (artery) 721 such that blood flow is significantly or completely impeded between the balloon and the vessel wall. The UV laser light is deployed in accordance with the methods described herein, such that an annular beam is emitted to contact the inner wall of the vessel, and the vessel partially dilates 722 (propagating in both directions from the area contacted by the UV laser annular beam.) The extraction procedure using a stentriever or, as shown by example only step E, an aspiration thrombectomy catheter 750 can be used in its conventional fashion to extract the thrombus 701, which is shown as removed from the middle cerebral artery 702 in step F. The dilation caused by the UV laser contact can facilitate the removal step(s).

Advantageously, the described method of dilation can provide diminished mechanical friction, thereby minimizing damage to the arterial wall. Another advantage is that the platelet component of a clot will also dilate (cf. U.S. Pat. No. 6,539,944) and that portion nearest the arterial wall partially degrade into individual platelets (by dethrombosis), and thus provide less adhesion to the wall and thus less frictional resistance to the process of extraction. No emboli will be produced.

In a method according to the subject invention, the UV light emission can be continuous for a short duration of time, such as 2-10 seconds, preferably about 5 seconds, or can be repeated so long as the optical path in either case is cleared of blood by balloon contact or by saline injection. The laser irradiation interval can be filled by a continuous wave laser beam, or by a beam which itself consists of a plurality of successive MHz mode-locked pulses (about 10 picoseconds in width), called a quasi-continuous beam, or by a plurality of successive 5-25 KHz pulses (up to 100 nanoseconds in width), called an acousto-optically Q-switched beam. The UV light is preferably directed onto the vessel wall within about 20 vessel diameters of the thrombus. More preferably, the UV light is directed onto the vessel wall within about 4 vessel diameters from the thrombus when using a balloon. In a preferred method, the vessel is an artery which is partially or fully occluded by a clot.

The UV light is emitted at a wavelength of about 180-400 nm and is preferably emitted at a wavelength of about 300-400 nm. In one preferred embodiment, the UV light is emitted using a frequency-tripled Nd:YAG laser which emits light at 355 nm. (Other Nd-containing crystals such as alexandrite also exist). NO. production has been measured to be maximum at 350 nm; however, laser UV light is currently not available at a wavelength of 350 nm, and a wavelength of 355 nm can be used with only a slight decrease in efficiency. Newly developed lasers at 349 nm and 360 nm exist but are not yet reliable enough to be used clinically. Other UV-producing lasers which can be used with the invention (but not to the point of ablation) include the XeF laser (351 nm) and continuous wave (CW) argon ion laser (351, 364 nm). Any diode laser or dye laser can also be used provided that an output can be obtained in the UV range required for the non-ablative vasodilation effect. Diode lasers are unable, at present, to produce wavelengths in the optimum region. However, if the physical difficulties in manufacturing are overcome, diode lasers could also be used and would be much smaller than the lasers proposed above. In principle, any laser can be used which emits UV radiation either directly or as the result of frequency doubling or tripling.

In a device or method of the invention, the average incident intensity of the UV light is between about 3 and about 20 watts per square centimeter (W/cm$^2$).

The device and method of the invention can be used in combination with the preadministration of a pharmaceutically acceptable thrombolytic agent which aids in thrombus dissolution (of fibrin). The concern is emission of clot fragments, which is avoided by our process of platelet dethrombosis. The preferred process of thrombectomy is to remove clots without the complication of fragmentation by the thrombolytic agent.

One particular embodiment introduces the laser beam through an endovascularly deployed optical fiber comprising a protruding (external) conical tip which by one reflection and one refraction can serve, in effect, as a diverging lens for the beam. This design will produce a circumferential irradiation pattern as an expanding conical ring, producing an annular beam of laser light on the wall of the tubular anatomical structure onto which the beam is directed. The protruding conical output tip is preferably made using a UV-transparent material with a higher index of refraction than fused silica, such as diamond, zirconium oxide, or a custom plastic with n>2, which can be optically coupled to the silica. As the beam exit angle is increased within the limits imposed by Snell's Law, beam intensity on the wall and efficiency of arterial dilation are increased because the distance to the wall, the width of the beam projected along the arterial wall, and thus the area irradiated, are all decreased.

These same considerations apply to the inverted conical tip as well, but the maximum emission angle will be less than that from the external tip. The intent is to provide two different ways to produce beams in the shape of an expanding ring, the relative benefits of which have been described above and can be assessed for clinical application A preferred optical fiber tip comprises an inverted tip configuration (FIG. 3), which is less likely to be obstructed during use, although its deployment through the guide catheter should avoid this possibility, as well as that of arterial perforation.

Another embodiment is a fused silica optical fiber with an externally projecting tip (FIG. 1B), with a maximum emission (half-conical) angle of ca. 48.4° (cf. Table 2.) When the tip is sharp (full apex conical angle is less than 40°, cf. FIG. 2A) it may be subject to fracture by mechanical contact if a fragile material is used. This situation can be remedied with an external conical tip made of a very hard material having a high refractive index, such as diamond. An everted diamond conical tip will permit an exit angle of up to 71.5°. Of course, with increasing bluntness (increased full conical apex angle), an external tip (including silica itself) will be more resistant to mechanical damage.

UV light, when absorbed by nitrites ($NO_2^-$) in the smooth muscle cells of the arterial wall, can release nitric oxide (NO.) in concentrations greater than those maintained by the endothelium during normal metabolism. This induces quasi-temporary (tens of minutes to hours) and semi-local dilation of the vessel. The release of NO. from the smooth muscle cells is self-propagated by transnitrosation along a localized distance of up to a few centimeters proximally and distally from the site of irradiation with UV light. A UV laser is used to induce vasodilation in the vicinity of the occlusion, thereby reducing friction with (or chemical bonding to) the arterial wall when a thrombectomy device is deployed to extract the blood clot. Thus, dilation of the vessel can facilitate separation of the clot from the vessel wall to which it is adhered, and facilitate easier and safer removal of the clot using a conventional aspiration catheter or stentriever (by lessening the intensity and frequency of its interaction with the vessel wall). This invention can advantageously reduce later-stage consequences of structural and functional damage to the endothelium and intimal structure of occluded arteries subjected to thrombectomy.

Dilation of the vessel increases the diameter of the vessel, which can also facilitate movement of the catheter into position, i.e., tortuosities (severe bends) or strictures of the vessel can be transited more easily.

To achieve the object of the invention, one novel aspect relates to an advantageous configuration for the tip of the optical fiber from or through which the UV irradiation is emitted. For example, it has been discovered that employing an external conical tip comprising a very hard but UV-transparent material, such as diamond, can more readily provide an external (half-conical) angle of emission up to 71.5° (with respect to the fiber axis) and a concomitantly narrower projection of the ring beam of the UV light. The preferred angle is best determined in association with other components (e.g., a UV-transparent balloon expanded with UV-transparent gadolinium-based contrast agent) of the system.

In another embodiment of the invention, the distal end of the optical fiber is capped with an inverted conical tip. The inverted conical tip preferably is comprised of a UV-transparent, high refractive index material such as diamond, zirconium oxide, or a custom plastic and is capable of emitting a ring beam at an angle of emission up to 56° (from diamond) relative to the longitudinal axis of the fiber.

It is another object of the invention to provide an optical fiber capable of transmitting UV light encompassed by a catheter, wherein the optical fiber is comprised of an inverted conical tip, preferably composed of a UV-transparent material such as diamond, zirconium oxide, or a custom plastic which is capable of emitting a ring beam for a cerebral artery. A narrow beam width will concentrate the amount of energy absorbed by the cells of the vessel so that an effective amount of NO. will be released for significant vessel dilation to occur, even if a relatively low power laser is used.

It is yet another object of the invention to provide a dilation system, which in the final step can include an aspiration catheter or stentriever, preceded by a balloon catheter encompassing a fused silica optical fiber capable of carrying UV light to the distal end of the catheter. Preferably the dilation system encompasses a fused silica optical fiber for UV irradiation with a conical tip at the distal end of the optical fiber. Preferably, the conical tip is comprised of a UV-transparent material with a high index of refraction such as diamond, zirconium oxide, or a custom plastic. More preferably, the conical tip is an everted conical tip configuration. Alternatively, the fused silica optical fiber component of the dilation system of the invention comprises a thrombectomy aspiration catheter or stentriever system which encompasses an optically contacted inverted conical tip comprised of an ultraviolet-transparent, high refractive index material such as diamond, zirconium oxide, or custom plastic.

It is still another object of the invention to provide a UV-transparent balloon catheter enveloping a UV-compatible optical fiber in combination with an aspiration thrombectomy catheter as part of unitary dilation system. Preferably, a UV-compatible optical fiber in combination with an aspiration thrombectomy catheter or stentriever will incorporate a diamond or zirconium oxide (or high refractive index plastic) everted conical tip at its distal end.

In one preferred embodiment, a balloon catheter can be expanded using a UV-transparent gadolinium-based contrast fluid; the balloon wall then displaces blood which results in a clear path for UV laser light to travel to the arterial inner wall. In accordance with the subject invention, the balloon is inflated for this purpose, and also to center the conical tip; it is not inflated to expand the inner diameter of the vessel wall. The gadolinium contrast agent is localized to the balloon and thus isolated from the blood stream. In this embodiment, the balloon material and the contrast material are sufficiently transparent to UV light to allow UV light to pass through the enveloping catheter and balloon unimpeded.

A further object of the invention is a method of performing a thrombectomy procedure in a mammal in need thereof, wherein the method comprises the steps of:
a) providing a dilation system as described herein
b) positioning the UV-fiberoptic thrombectomy catheter within one to four vascular diameters of a clot within an occluded vessel;
c) emitting a square-wave pulse of continuous or high repetition-rate pulsed beam UV laser light energy as a beam within a specified average intensity range onto smooth muscle cells lining the inner wall of the vessel to release NO. from the cells and thereby cause dilation of the vessel; and
d) removing the clot by mechanical extraction.

In one embodiment, the UV-fiberoptic dilation system preferably features a fused silica fiber with a diamond conical tip capable of emitting a ring beam at an angle of up to 71.5° (for an external tip) relative to the longitudinal axis of the fiber. This angle will be less for other known high-index materials such as zirconia and custom plastics.

The burst of UV light energy, in continuous or pulsed form, can be emitted for an irradiation interval of about 2-20 seconds, preferably at least about 5-15 seconds, and more preferably about 8-12 seconds. A 10-second burst can be a most preferred duration of emission of the UV light beam for dilating the vessel to sufficient diameter to lessen frictional interaction of the catheter with a vessel tortuosity or stricture, or to facilitate separation of the clot from the vessel wall.

In a preferred embodiment, the invention comprises a dilation system comprising either an aspiration catheter or a stentriever following a preparatory period which employs a conical-tipped optical fiber supplying a ring-shaped beam of UV irradiation. The conical tip of the optical fiber can project inwardly or outwardly from the distal end of the optical fiber, depending on the angle of emission desired and presence or lack of obstacles along the desired path.

In use, the optical fiber comprising a conical tip can emit a conical beam locus which irradiates the tubular anatomical structure as an annular or ring-shaped beam around the inner circumference of the tubular structure. Tubular anatomical structures that can be dilated with UV light are those that are lined with (smooth muscle) cells capable of storing (as nitrites) and releasing nitric oxide (NO.). This dilation can advantageously be used to expand or dilate an artery at a position near a thrombus to facilitate easier and safer removal of the thrombus by reducing mechanical friction. The thrombus can be an occlusive thrombus or a non-occlusive thrombus. Vasodilation at the site or in the vicinity of a thrombus within the vessel can loosen the adhesion of the thrombus to the vessel wall or separate the thrombus from the vessel wall, thereby facilitating efficient removal of the thrombus by conventional aspiration or stentriever catheter techniques currently used in the medical field. Peripheral injury to the occluded vessel should be minimized before, during, and after the extraction.

Dilation of the artery in the area of the thrombus can occur when irradiation with UV light occurs within about 1, 2, 3, 4, 5, 6, 7, 8, 9, 10, 12, 14, 16, 18, 20, 25, or 30 vessel diameters of the thrombus. As used herein, the term "vessel diameter" refers to the outer diameter of an artery. Preferably, the vessel is irradiated within about 10 vessel diameters of the thrombus. More preferably, the vessel is irradiated between about 1 and 4 vessel diameters removed from the thrombus. The vessel can be irradiated proximal to or distal to the thrombus.

A branch vessel can also be dilated by irradiating the trunk vessel at a distance of about 3, 4, 5, 6, 7, 8, 9, 10, 12, 14, 16, 18, 20, 25, or 30 vessel diameters from the thrombus because the UV-induced vasodilation effect can propagate distally (as well as proximally). This phenomenon can be especially useful in cases where a surgeon does not have feasible access to a branch vessel containing a thrombus but does have proximal access to the trunk vessel.

Preferably, the UV light beam is directed onto the inner surface of a tubular anatomical structure, such as an artery, by a beam transmitted through an optical fiber placed inside the vessel by means of a catheter. Subsequent to irradiation, but almost immediately thereafter, and no longer than within a few seconds of irradiation with the laser beam, the vessel dilates, first at the irradiated portion and then continuously self-propagates for a distance of several centimeters in the proximal and distal directions.

Under normal physiological conditions, dilation is mediated by nitric oxide (NO.) produced by the endothelium. In contrast, UV laser-mediated photophysical production of NO. results from photoscission of nitrites ($NO_2^-$) stored in undamaged smooth muscle cells in the arterial wall. Local NO. concentrations of up to 10 μM can be produced regardless of the severity of endothelial damage or even when endothelium is absent (totally destroyed).

Nitrite photolysis in smooth muscle cells yields NO., S-nitrosation of thiols (RSHs) leading to S-nitrosothiol (RNSO) formation, and local dilation via NO. or its release from thionitrates (RSNOs); these transnitrosate other thiols, propagating the dilation radially, distally, and proximally by more release of NO. This is a self-perpetuating chain process.

Nitric oxide produced photophysically can stimulate a wave of dilation both proximally and distally. Thus, it is possible for frictional resistance to clot removal to be decreased over some fraction of the length of the clot. The clot can thus be extracted with less force, and therefore, less mechanical damage to the artery than that currently observed, with fewer future complications at the site or distal or even proximal to it.

Laser beams used to dilate an artery, and thereby treat occluded vessels, can be either continuous or pulsed. Use of a pulsed laser reduces heat buildup and consequent damage in the target and surrounding tissues. If a non-ablative pulsed laser, such as a quasi-continuous or acousto-optic Q-switched laser is used, the pulse rate can be any rate consistent with delivery of an appropriate time-averaged intensity of irradiation to the target tissue, while avoiding individual pulses of such high intensity that lasting damage, i.e., damage which is irreversible in a physiologically relevant time frame (e.g., a period of hours to weeks), results in the target tissue.

The UV light is preferably in the range of 180-400 nm in wavelength. More preferably the UV light is in the range of 300-400 nm. Even more preferably the UV light is about 340-370 nm, and most preferably it is about 350-360 nm. A frequency-tripled Nd:YAG laser emitting radiation of 355 nm is especially preferred.

Other UV lasers which can be used with the invention (while avoiding ablation) include the XeF laser (351 nm), CW argon ion (351, 364 nm) or CW krypton ion (351, 356 nm). Any diode laser or dye laser can also be used provided that a non-ablative output can be obtained in the UV range required for the vasodilation effect. In principle, any laser can be used which emits UV radiation either directly or as the result of frequency doubling or tripling.

For 355 nm UV laser irradiation, dilation is stimulated over a wide dynamic range of 7 for intensities, 3 to about 20 $W/cm^2$ in intensity, assuming a gaussian beam shape. The dilation effect, however, is independent of beam shape. At the upper limit, vacuoles are formed in smooth muscle cells, but functionality is undamaged. The dilation effect is dependent on the average intensity. For example, a 7 Hz train of 100 nsec pulses with 5 kilowatt peak power can be used at 20 $W/cm^2$ without inducing functional damage.

Blood can be cleared from the path of the laser beam, for example, by flushing a small amount of physiological saline solution through the opening of the catheter from which the beam exits immediately prior to illuminating the vessel wall or thrombus.

The intensity of UV illumination is preferably adjusted to provide the minimal dose required to achieve the desired extent of vasodilation within the desired timeframe prior to thrombectomy. For example, using a frequency tripled Nd-YAG laser, an incident intensity of about 5 watts/$cm^2$ produces a dilation of ~20-30% in small arteries (this dilation is reversible by a NO inhibitor drug). Higher intensities of 12-20 watts/$cm^2$ (equivalent to an energy fluence of up to 1 J/$cm^2$ per pulse at a pulse rate of 20 Hz) can produce a similar increase in diameter of larger arteries (ca. 1.5 mm diameter) but intensities in excess of 20 watts/$cm^2$ may alter vascular wall structure (small vacuoles are formed in the smooth muscle tissue), but functional damage is not observed.

The incident intensity can then be increased in increments (e.g., increments of 2 watts/$cm^2$ or larger) until suitable dilation of the vessel is observed within a reasonable time, e.g., within 5 seconds. The period of irradiation can be continuous, i.e., lasting until the dilation effect plateaus, or can be intermittent, in which case the duration of one or more periods of irradiation can also be varied at a given incident intensity in order to obtain an appropriate response; the dilation already elicited will be preserved and amplified. The appropriate vasodilation response, i.e., extent of dilation and its kinetics of onset and duration, can be determined by the user; however, responses in the range of 20-40% increase in vessel diameter over 5-10 seconds would generally be regarded by many users as appropriate.

The method of the present invention is suitable for treating a variety of disease conditions which involve occlusion of an artery. Examples of such conditions include stroke, myocardial infarction, and occlusion or spasm of any peripheral artery, large or small.

In a method of the invention using an aspiration catheter, a balloon catheter can be introduced and then the aspiration catheter just over the catheter and behind the balloon portion. The UV fiber can then be introduced into the balloon. When the UV-transparent balloon is dilated to just exceed the diameter of the aspiration catheter ahead of tortuous bends or strictures, the UV fiber is then centered in the artery and the nonflowing blood is displaced from the projected light path. Then the UV beam can be flashed for several seconds to get dilation sufficient to permit passage of the thrombectomy catheter used in the subject dilation system. Here the balloon does not push against the artery to dilate it, but only facilitates a means to displace blood away from it while the laser ring beam follows an optically free path to dilating the artery non-mechanically. Balloons are very common but can do damage if overinflated.

Once the UV light is emitted onto the wall of the vessel and absorbed, the vessel will dilate and propagate dilation regardless of the subsequent presence of blood or blood flow. This process can be utilized to traverse tortuous bends or strictures more easily on the way to the clot. Accordingly, structural, and endothelial damage is minimized from the entry point to the target location. Once at the clot, a final irradiation is made, including an optional saline flush, and then the aspiration catheter extracts the clot.

For use in combination with a stentriever, the guidewire penetrates and is moved past the clot by a few centimeters. The balloon catheter is then inserted to center the guidewire in the distal segment and is dilated as described above and flushed just enough to displace static blood. The guidewire is withdrawn and replaced by the UV fiber which irradiates the cleared arterial segment for 5-10 seconds just distal to the clot. After dilation, the UV fiber is withdrawn and the stentriever replaces it through the balloon catheter. The stentriever is now centered and the balloon catheter can be withdrawn. The stentriever is expanded to a diameter larger than the artery which enables it to better ensnare the entire clot and ensure extraction efficiency.

Another benefit is the capability to employ UV irradiation at locations difficult to traverse by catheter toward the target clot location; this will facilitate safer clot extraction. Catheters that appear too large for an artery at some unexpected point can still be used following UV dilation. If a catheter size selection mistake is made at the outset, UV dilation can be used to dilate the artery without having to replace the current catheter.

The design of an external projecting conical tip ($\alpha=18°$, FIGS. 1A, 1B and 2A) using a silica optical fiber was developed for endovascular deployment via microcatheter.

TABLE 1

Emission angle $\beta(\alpha)$ in degrees for 355 nm light emitted from a silica optical fiber ($n_1 = 1.475$) with an external conical tip into water ($n_2 = 1.333$) or air ($n_2 = 1.00$); $\alpha$ = half-angle at apex of conical tip; $\beta(\alpha) = \pi/2 - \alpha - \gamma(\alpha)$, $\delta = \pi/2 - 3\alpha$, and $\gamma(\alpha) = \sin^{-1}\{(n_1/n_2) \cos 3\alpha\}$.

| $\alpha$ | $\beta(\alpha_{water})$ | $\delta(\alpha_{water})$ | $\gamma(\alpha_{water})$ | $\beta(\alpha_{air})$ | $\gamma(\alpha_{air})$ |
|---|---|---|---|---|---|
| 25 | 48.35 | 15 | 16.64 | | |
| 22 | 41.62 | 24.0 | 26.38 | 31.13 | 36.87 |
| 21 | 39.27 | 27.0 | 29.73 | 26.96 | 42.04 |
| 20.5 | 37.63 | 28.5 | 31.87 | 24.77 | 44.73 |
| 20 | 36.89 | 30.0 | 33.11 | 22.48 | 47.52 |
| 19.5 | 35.18 | 31.5 | 35.32 | 20.08 | 50.42 |
| 19 | 34.48 | 33.0 | 36.52 | 17.55 | 53.45 |
| 18.5 | 33.27 | 34.5 | 38.23 | 14.84 | 56.66 |
| 18 | 32.04 | 36.0 | 39.96 | 11.89 | 60.11 |
| 17.5 | 30.81 | 37.5 | 41.69 | 8.61 | 63.89 |
| 17 | 29.56 | 39.0 | 43.44 | 4.84 | 68.16 |
| 16.48 | 28.26 | 40.55 | 45.26 | ~0 | 73.52 |
| 16 | 27.02 | 42.0 | 46.98 | TIR | |

Note:
the limit of $\alpha$ is (90° − the critical angle of 64.653° for glass to water) = 25.347°.

To increase $\beta$ (and thus decrease the area subtended on the arterial wall by the ring beam), a short (ca. 0.5 mm) everted conical segment made from a UV-transparent material with a higher index of refraction must be optically bonded to the silica fiber. The optimum choice is diamond, with an index of refraction of $n_d=2.48$.

Table 2 presents the same calculation as above for a beam exiting into water from an external diamond tip.

TABLE 2

Emission angle $\beta(\alpha)$ in degrees for 355 nm laser light emitted from an external diamond-tipped silica optical fiber ($n_1 = 2.48$) into water ($n_2 = 1.333$) (cf. FIG. 3); $\beta(\alpha) = 90 - \alpha - \gamma(\alpha)$, $\delta = 90 - 3\alpha$, and $\gamma(\alpha) = \sin^{-1}\{(n_1/n_2) \cos 3\alpha\}$, where $\alpha$ = half-angle at apex of conical tip.

| $\alpha$ | $\beta(\alpha_{water})$ | $\delta(\alpha_{water})$ | $\gamma(\alpha_{water})$ |
|---|---|---|---|
| 20.2 | 3.83 | 29.4 | 65.97 |
| 21 | 11.37 | 27 | 57.63 |
| 22 | 18.83 | 26 | 49.17 |
| 23 | 25.19 | 21 | 41.81 |
| 24 | 30.91 | 18 | 35.09 |
| 27 | 46.08 | 9 | 16.92 |
| 29 | 55.41 | 3 | 5.59 |
| 30 | 60 | 0 | 0 |
| 31 | 64.87 | −3 | −5.87 |
| 32.5 | 71.55 | −7.5 | −14.05 |

Note:
the critical angle of incidence for total internal reflection (diamond to water) is 32.51°.

Table 3 shows the range of paths of 355 nm laser light emitted into water (saline) toward the arterial wall from inverted conical tips made from silica and diamond. The emission angle $\beta$ is a function of the inverted cone half-angle $\alpha$ (depicted in FIG. 3) An inverted conical tip design may be preferred by some practitioners, because the entrapment of the tip in an obstruction, if any, is much less likely than with an external conical tip.

TABLE 3

Emission angle $\beta$ in degrees, calculated from Snell's Law as a function of the inverted cone half-angle $\alpha$ for silica and diamond tips for ring beams emitted into water toward the arterial wall (FIG. 3). $\alpha = 90° - \theta_1$, where $\theta_1 = \theta_{g,d}$ and g = glass (silica), d = diamond, $\theta_2 = \theta_{water}$ and $\beta = \theta_{water} - \theta_{s,d}$.

| Silica Fiber, $n_{glass}$ | | | | Diamond-tipped Silica Fiber, $n_{diamond}$ | | | |
|---|---|---|---|---|---|---|---|
| $\theta_{glass}$ | $\theta_{water}$ | $\alpha$ | $\beta$ | $\theta_{diamond}$ | $\theta_{water}$ | $\alpha$ | $\beta$ |
| 64.60 | 88.31 | 25.40 | 23.71 | 32.50 | 88.44 | 57.50 | 55.94 |
| 60.00 | 73.39 | 16.61 | 13.39 | 31.50 | 76.43 | 58.50 | 44.93 |
| | | | | 31.00 | 73.38 | 59.00 | 42.38 |
| | | | | 30.00 | 68.47 | 60.00 | 38.47 |

This calculation complements those done on the external diamond conical tip, and shows that the emission angle $\beta$ is even larger and thus provides increased beam intensity at a decreased distance from external conical tip compared to the inverted conical tip (either is much preferable to silica alone). However, $\beta$ is remarkably sensitive to $\alpha$, which means that the input beam must be well collimated to minimize the polar angle spread $2\theta_w$ (cf. FIG. 1A) and that the internal conical tip must be ground very precisely to ensure high surface quality and thus minimize beam scattering. Here, $\theta_{crit}=\theta_{diamond}=32.51°$ and $\beta=57.49°$. If $\theta_{diamond}=32.50°$, then $\theta_{water}=88.44°$, $\alpha=57.50°$, and $\beta=55.94°$ (Table 3).

As an alternative to the conical-tip optical designs shown so far to produce a ring beam, we propose a combination of diffractive optics with optical fibers. Diffractive optics involves etching a geometric pattern by any of several methods (e.g., lithography, electron beam evaporation) on a flat-ended optical fiber, the tip of which can be fused silica itself or other optically coupled UV-transparent, high refractive index (n>2) substances such as zirconia, diamond, or a custom designed plastic, to obtain the desired diffractive phase profile. The pattern on the end of the fiber resembles a circularly symmetric bas-relief sculpture—a series of concentric annular structures variable in depth and radius, as material must be removed with precision to make the desired diffractive phase profile. The desired output is a very sharp ring-shaped Bessel beam with minimal sidebands. For beams exiting the tip at angles $\beta > 40°$, it is likely that high refractive index substances such as the latter three (as already illustrated) be used. Ring beams with greater than $\beta = 15°$ by this technique in any medium have not yet been produced, to our knowledge, but manufacturers of diffractive optical devices are open to expanding the range of their capabilities. A flat-end diffractive pattern emplaced on a suitable high-index material, which comprises the end cap of a fused silica optical fiber immersed in water, might be the optimal form of the device.

Either an external or internal conical tip can produce a ring beam at a range of angles to the arterial wall, for external tips the upper limit is 48° for silica and 71.5° for diamond, but preferably the maximum angle will be used. For an internal diamond conical tip, the range can be up to 56°, which is preferred. The immediate benefit of emitting the beam at a maximum acute angle is reduced ring beam width and thus higher laser intensity. Because the dilation process is entirely dependent on beam intensity (between 3 and 20 watts/cm$^2$), a lower power (and likely more compact) laser can be used more efficiently. The internal conical tip was designed in the interest of safety because in previous work we noticed that a silica external tip could be damaged. Presentation of a device which will not be damaged upon insertion by attachment to any other device or tissue component is obviously beneficial, because entrapment is avoided, and tip structure is preserved. However, these effects are unlikely to occur in a very hard material such as diamond.

These and other embodiments and applications of the invention will become apparent to the skilled artisan in view of the description provided herein. A common but refractory aspect of hemorrhagic stroke is vasospasm (constriction) of a major cerebral artery. Blood emitted into (for example) the subarachnoid space from a ruptured aneurysm migrates along the artery, and hemoglobin from lysed red blood cells enters the arterial wall and scavenges nitric oxide, thus inducing the spasm. This condition cannot be treated reliably at present; any systemic dilator drug will lower blood pressure to the point of morbidity. Another aspect, untreatable at present, is early brain injury (i.e., preceding vasospasm) mediated by platelet-occluded microvessels in brain. Despite much animal research, there is no drug which will dissolve platelet thrombi in humans. The UV laser method is intended to treat both of these extremely difficult conditions unequivocally. We have shown reversal of vasospasm at three days in dogs subjected to hemorrhagic stroke. We also showed that platelet clots can indeed be dissolved by UV laser-induced nitric oxide, because it inhibits thrombin, an enzyme required to maintain inter-platelet fibrinogen/platelet GPIIb-IIIa cross-links.

We propose that UV irradiation of a feeder artery just proximal to its connection with distal branches and their microvascular beds will enable reperfusion of blood, not just arterial recirculation, owing to the self-replication of nitric oxide over distance and its associated vasodilation, thus improving the likelihood of tissue survival. For example, a patient with a ruptured brain aneurysm will be emergently treated by standard of care interventional devices such as coils and stents. After the aneurysm is secured, the neuro-interventionalist may then proceed to position the micro-catheter used for coiling farther distal to the aneurysm. The micro-catheter can be replaced with a UV-transparent balloon catheter and the micro-guidewire replaced with an optical fiber. Distal UV irradiation will dissolve platelet embolus-occluded microvessels in the vascular territory thereby enhancing reperfusion and improving clinical outcomes for the patient. Three to twenty-one days after the aneurysm treatment, cerebral vasospasm may cause vascular constriction. Again, using a UV-transparent balloon catheter and optical fiber, UV irradiation proximal to the vascular constriction will dilate and restore the artery to its original (or greater than original) diameter, thereby restoring blood circulation.

Atherosclerotic vascular disease can cause stenosis or narrowing (stricture) of arterial lumens due to the formation of plaque. Present methods call for enlargement of the lumen by balloon angioplasty, followed by stenting to secure the opening. Angioplasty and stenting first require that a micro-guidewire be passed through the stenosis to get distal access. When the stenosis is moderate to severe, it is difficult to pass a guidewire through the stenosis safely without dislodging the atheroma. During stenting procedures for atherosclerotic disease, passage of guidewires and devices through the plaque can be facilitated by dilating the artery with UV. If the plaque is calcified, it may be very hard and incompressible. Also, balloon expansion may cause adjacent non-atheromatous segments to expand and stretch even to the point of structural distortion. A common response to such trauma is hypertrophy, an abnormal healing response which is known to eventually occlude the opening made by the stent. We propose that non-mechanical dilation of an artery, even a diseased one, by the nitric oxide pathway will substantially facilitate distal access of the atheroma with endovascular devices. The NO pathway will also minimize vascular distortions and overexpression of the healing response, and thus preserve the desired lumen and its useful lifetime. Endothelial damage in adjacent non-atheromatous segments will also be reduced. For example, in a patient with severe carotid atherosclerosis, a UV-transparent balloon catheter can be positioned proximal to the stenosis with the aid of a micro-guidewire. The guidewire can be replaced with an optical fiber. Subsequent UV irradiation will expand the arterial wall and widen the stenosis gap. The optical fiber can then be replaced with the micro-guidewire and the guidewire can now be more easily navigated through the widened stenosis to get distal access. The balloon catheter can then be removed, and a device delivery system passed over the guidewire for treatment of the plaque. The same system can be used in general to emplace a stent safely to ensure circulation through a stricture, except now the stent can be emplaced in the dilated vessel without causing endothelial damage. This will avoid restenosis, a very common complication of stent deployment as currently practiced, and the need to replace the stent within 3-5 years.

Inhaled nitric oxide can be used, especially in pediatric patients, to treat pulmonary hypertension and acute respiratory distress syndrome. The inhaled gas diffuses through the alveolar-capillary membrane and causes vasodilation resulting in reduced pulmonary vascular resistance and increased blood perfusion in ventilated lung segments. This potentially improves blood oxygenation in the patients. The proposed invention can potentially be used in a more targeted manner to vasodilate segments and branches of the pulmonary artery. The pulmonary artery and its branches can be accessed through the femoral vein via catheterization of the right heart. A balloon catheter can then be positioned in the targeted pulmonary artery branch. The optical fiber can be introduced into the inflated balloon in order to irradiate the arterial wall with a ring beam. The resulting vasodilation will propagate itself proximally and distally from the area contacted by the annular beam via transnitrosation.

The above disclosure and example generally describe the present invention and is provided for purposes of illustration and is not intended to limit the scope of the invention. The invention described herein may be practiced in the absence of any element or elements, limitation or limitations which is not specifically disclosed herein. Thus, for example, in each instance herein, any of the terms "comprising," "consisting essentially of," and "consisting of" may be replaced with either of the other two terms. The terms and expressions are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the claims.

The invention claimed is:

1. A dilation system for dilating a tubular anatomical structure using UV laser light, said dilation system comprising an optical fiber and a UV laser light source, the optical fiber having a distal end configured as an external projecting cone shape and capable of emitting the UV laser light as a conical beam and emitting into water an annular beam at an emission angle β up to 71.5° from a central longitudinal axis of the optical fiber.

2. The dilation system of claim 1, wherein the dilation system includes a balloon catheter.

3. The dilation system of claim 2 wherein the optical fiber is centered within the balloon catheter.

4. The dilation system of claim 1, wherein the optical fiber distal end comprises a tip configured as an external projecting cone, said tip being coupled to the optical fiber and in optical communication therewith.

5. The dilation system of claim 1, wherein the dilation system includes a thrombectomy device.

6. A method for dilating a tubular anatomical structure in a body of a patient, said method comprising:
   providing a dilation system comprising a catheter housing, an optical fiber for carrying UV laser light from a UV laser light source, wherein the optical fiber has a distal end selected from an external projecting cone configuration and an inverted cone configuration, wherein the external projecting cone configuration is capable of emitting the UV laser light as a conical beam and emitting into water an annular beam at an emission angle β up to 71.5° from a central longitudinal axis of the optical fiber, and the inverted cone configuration is capable of emitting the UV laser light as a conical beam and emitting into water an annular beam at an emission angle β 20° to 56° from a central longitudinal axis of the optical fiber;
   emitting from the distal end of the optical fiber, UV laser light energy as an annular beam onto smooth muscle cells of an inner wall of the tubular anatomical structure to stimulate a production and release of nitric oxide (NO) from stores of nitrites ($NO_2^-$) in the smooth muscle cells, whereby the nitric oxide causes relaxation of the smooth muscle and dilation of the tubular anatomical structure.

7. The method of claim 6, wherein the anatomical structure in a body of a patient is selected from an anatomical canal, an anatomical tube or tubule, a blood vessel, a bronchiole, a ureter, and a vas.

8. The method for dilating a tubular anatomical structure in a body of a patient of claim 6, wherein the method is applied in an endovascular thrombectomy procedure employing a thrombectomy device wherein the method further comprises the steps of:
   positioning the UV optical fiber within about 1-10 vessel diameters of a clot within an artery and centered within the diameter of the artery;
   emitting a burst of UV light energy as a laser beam onto smooth muscle cells on an inner wall of the artery to stimulate production of nitric oxide (NO) from stores of nitrites ($NO_2^-$) in the smooth muscle cells, whereby dilation of the artery results; and
   removing the clot.

9. The method of claim 8, wherein the thrombectomy device is an aspiration catheter.

10. The method of claim 8, wherein the thrombectomy device is a stentriever.

11. The method of claim 6, wherein the optical fiber is centered using a balloon catheter.

12. The method of claim 11, wherein the balloon catheter is transparent to UV light.

13. The method of claim 6, wherein the UV light is directed onto the arterial wall within about 1 and about 4 vessel diameters from the clot.

14. The method of claim 6, wherein the UV light is pulsed at high frequency of 5-25 kHz with greater than 50 nanosecond pulse width, or as a quasi-continuous 100 MHz beam with about 10 picosecond pulse widths, or as a continuous square wave for at least 2 seconds and up to 10 seconds.

15. The method of claim 6, wherein the UV light is emitted at a wavelength of about 180-400 nm.

16. The method of claim 6, wherein the UV light is emitted at a wavelength of about 300-400 nm.

17. The method of claim 6, wherein the UV light is emitted using a frequency-tripled Nd:YAG laser which emits light at 355 nm.

18. The method of claim 6, wherein the incident intensity of the UV light is between about 3 and about 20 watts per square centimeter.

19. The method of claim 6, wherein the conical tip is configured as an inverted cone.

20. The method of claim 6, wherein the conical tip is configured as an everted or external projecting cone.

21. A dilation system for dilating a tubular anatomical structure using UV laser light, said dilation system comprising an optical fiber and a UV laser light source, the optical fiber having a distal end configured as an inverted cone shape and capable of emitting the UV laser light as a conical beam and emitting into water an annular beam at an emission angle β of 20° to 56° from a central longitudinal axis of the optical fiber.

22. The dilation system of claim 21, wherein the dilation system includes a balloon catheter.

23. The dilation system of claim 22 wherein the optical fiber is centered within the balloon catheter.

24. The dilation system of claim 21, wherein the optical fiber distal end comprises a tip configured as an inverted cone coupled to the optical fiber and in optical communication therewith.

25. The dilation system of claim 21, wherein the dilation system includes a thrombectomy device.

* * * * *